(12) United States Patent
Reichlin et al.

(10) Patent No.: US 6,280,944 B1
(45) Date of Patent: *Aug. 28, 2001

(54) ASSAY FOR PATHOGENICITY OF ANTI-DNA ANTIBODIES

(75) Inventors: Morris Reichlin; Eugen Koren; Wei Zhang, all of Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/366,103

(22) Filed: Aug. 2, 1999

Related U.S. Application Data

(63) Continuation of application No. 08/450,188, filed on May 25, 1995, now abandoned, which is a continuation-in-part of application No. 08/249,387, filed on May 25, 1994, now Pat. No. 5,681,700.

(51) Int. Cl.[7] ............... C12Q 1/68; G01N 33/53; G01N 33/567; G01N 33/537; G01N 33/543

(52) U.S. Cl. ............... 435/6; 435/7.1; 435/7.21; 435/7.92; 436/811

(58) Field of Search ............... 435/6, 7.1, 7.21, 435/7.92; 436/811

(56) References Cited

U.S. PATENT DOCUMENTS

| | | |
|---|---|---|
| 5,407,833 | 4/1995 | Van Regenmortel et al. . |
| 5,616,685 | 4/1997 | Van Venrooij et al. . |

FOREIGN PATENT DOCUMENTS

| | | |
|---|---|---|
| 0 276 984 A2 | 8/1988 | (EP) . |
| 0 295 719 A3 | 12/1988 | (EP) . |
| 0 307 858 A2 | 3/1989 | (EP) . |
| 0 313 156 A1 | 4/1989 | (EP) . |
| 0 438 259 A1 | 7/1991 | (EP) . |
| 2 682 113 A1 | 4/1993 | (EP) . |
| WO 90/10229 | 9/1990 | (WO) . |
| WO 95/32430 | 11/1995 | (WO) . |

OTHER PUBLICATIONS

Reichlin et al.; Lupus autoantibodies to native DNA . . . ; J. Clin. Invest.; vol. 93; pp. 443–449, Jan. 1994.*
Ter Gorg et al.; Changes in levels of antibodies against the 70–kDa . . . ; J. Rheumatol.; 18 (3); pp. 363–367, 1991.*
Ravirajan et al.; Antigen–binding diversity of human hybridoma autoantibodies . . . ; Lupus; ! (3); pp. 157–156, May 1992.*
Aarden, et al., "Immunology of DNA. II. *Crithidia luciliae*, a simple substrate for the determination of Anti–dsDNA with the immunofluorescence," *Ann. NY Acad. Sci.* 254:505–515 (1975).
Abdou, et al., "Network Therapy in Autoimmunity," *J. Clin. Invest.* 67:1297–1304 (1980).
Barada, et al., "Antibodies to Sm in patients with systemic lupus erythematosus. Correlation of Sm antibody titers with disease activity and other laboratory parameters," *Arthritis Rheum.* 24(10):1236–44 (1981).
Baxter Diagonostic Inc., p. 334 (1991/2).
Beaulieu, et al., "IgG antibodies to double–stranded DNA in systemic lupus erythematosus sera. Independent variation of complement fixing activity and total antibody content," *Arthritis Rheum.*, 22(6):565–70 (1979).
Boehringer Mannheim Biochemicals Catalog, pp. 308–312 (1991).
Borel & Borel, "Oligonucleotide linked to human gamma-globulin specifically diminishes anti–DNA antibody formation in cultured lymphoid cells from patients with systemic lupus erythematosus," *J Clin Invest.* 82(6):1901–7 (1988).
Borel, et al., "Prevention of murine lupus nephritis by carrier–dependent induction of immunologic tolerance to denatured DNA," *Science*, 182:76–77 (1973).
Borel, et al., "Treatment of lupus nephritis in adult (NZB+NZW)F1 mice by cortisone–facilitated tolerance to nucleic acid antigens," *J Clin Invest.* 61(2):276–86 (1978).
Caccavo, et al., Anti–idiotypes against antiphospholipid antibodies are present in normal polyspecific immunoglobulins for therapeutic use, *J Autoimmun.* 7(4):537–48 (1994).
Clackson, et al., "Making antibody fragments using phage display libraries," *Nature.* 352(6336):624–8 (1991).
Clark, et al., "Characterization of a soluble cytoplasmic antigen reactive with sera from patients with systemic lupus erythmatosus," *J. Immunol.* 102:117–120 (1969).
Daugherty, et al., "Polymerase chain reaction facilitates the cloning, CDR–grafting, and rapid expression of a murine monoclonal antibody directed against the CD 18 component of leukocyte integrins," *Nucl. Acids Res.*, 19:2471–2476 (1991).
Divalerio, et al., "Anti–DNA Antibodies can react specifically with DNA in the context of Glomeruli," *Clin. Res.*, 42:139A (1994).
Dwyer, et al., "Naturally occurring anti–idiotypic antibodies in myasthenia gravis patients," *Nature.* 301(5901):611–4 (1983).

(List continued on next page.)

*Primary Examiner*—Brett Nelson
(74) *Attorney, Agent, or Firm*—Arnall Golden & Gregory, LLP

(57) ABSTRACT

Assays that are prognostic for patients that will develop nephritis have been developed where patient serum is screened for the presence of anti-dsDNA antibodies that are cross reactive with A and D SnRNP proteins. The assays are based on the use of either peptides containing epitopes bound by the anti-dsDNA antibodies, or the antigens for the antibodies, A and D SnRNP proteins. Therapeutic compositions have also been developed using either antibodies that block the pathogenicity of the anti-dsDNA antibodies, such as the naturally occurring anti-La/SSB, anti-Ro/SSA and anti-$U_1$RNP antibodies that are cross reactive with the anti-dsDNA or using the peptides or A and D proteins to induce tolerance.

4 Claims, 2 Drawing Sheets

OTHER PUBLICATIONS

Geysen, et al., "Use of peptide synthesis to probe viral antigens for epitopes to a resolution of a single amino acid," *Proc Natl Acad Sci U S A*. 81(13):3998–4002 (1984).

Hahn and Tsao, Antibodies to DNA. –Tn Dubois, Systemic Lupus Erythematosus. D–J. Wallace and B. H. Hahn, editors. (Lea and Febiger, Philadelphia, PA 1993) pp. 195–201.

Hamilton, et al., "Two Ro (SS–A) autoantibody responses in systemic lupus erythematosus. Correlation of HLA–DR/DQ specificities with quantitative expression of Ro (SS–A) autoantibody," *Arthritis Rheum*. 31(4):496–505 (1988).

Handwerger, et al., "Palmerston North Mice Produce Antibodies to $U_1RNP$ and SM Particles," *Clin. Res*. 42:315A (1994).

Harley, et al. "A model for disease heterogeneity in systemic lupus erythematosus. Relationships between histocompatibility antigens, autoantibodies, and lymphopenia or renal disease," Arthritis Rheum. 32(7):826–36 (1989).

ICN Catalog, p. 161 (1992 May 1993).

Jacob, et al., "A monoclonal anti–DNA antibody also binds to cell–surface protein(s)," *Proc Natl Acad Sci U S A*. 81(12):3843–5 (1984).

Kabat, H.A., et al.I, *Sequences of Proteins of Immunological Interest, 4th Ed.* (U.S. Dept. health and Human Services, Bethesda, MD, 1987).

Koffler, et al., "Antibodies to polynucleotides in human sera: antigenic specificity and relation to disease," *J Exp Med*. 134(1):294–312 (1971).

Koren, et al., "Autoantibodies to the Ribosomal P Proteins React with a plasma membrane–related target on human cells," *J. Clin. Invest*. 89:1236–1241 (1992).

Lefvert, "Anti–idiotypic antibodies against the receptor antibodies in myasthenia gravis," *Scand J Immunol*. 13(5):493–7 (1981).

Lundberg, et al., "Clinical manifestations and anti–(U1)snRNP antibodies: a prospective study of 29 anti–RNP antibody positive patients," *Br J Rheumatol*. 31(12):811–7 (1992).

Maddison & Reichlin, "Deposition of antibodies to a soluble cytoplasmic antigen in the kidneys of patients with systemic lupus erythematosus," *Arthritis Rheum*. 22(8):858–63 (1979).

Maddison, et al. "Patterns of clinical disease associated with antibodies to nuclear ribonucleoprotien," *J Rheumatol*. 5(4):407–11 (1978).

Mattioli & Reichlin, "Heterogeneity of RNA protein antigens reactive with sera of patients with systemic lupus erythematosus. Description of a cytoplasmic nonribosomal antigen," *Arthritis Rheum.* 17(4):421–9 (1974).

Mattioli & Reichlin, "Characterization of a soluble nuclear ribonucleoprotein antigen reactive with SLE sera," J Immunol. 107(5):1281–90 (1971).

Miniter, et al., "Reassessment of the clinical significance of native DNA antibodies in systemic lupus erythematosus," *Arthritis Rheum*. 22(9):959–68 (1979).

Muryoi, et al., "Heterogeneity of anti–idiotypic antibodies to anti–DNA antibodies in humans," *Clin Exp Immunol*. 71(1):67–72 (1988).

Nisonoff, et al., "Separation of univalent fragments from the bivalent rabbit antibody molecule by reduction of disulfide bond," *Arch. Biochem. Bioshys*. 89:230–244 (1960).

Pasquali, et al., "Idiotypic network: possible explanation of seronegativity in a patient with rheumatoid arthritis," *Clin Exp Immunol*. 55(2):281–6 (1984).

Pennebaker, et al. "Immunoglobulin classes of DNA binding activity in serum and skin in systemic lupus erythematosus," *J Clin Invest*. 60(6):1331–8 (1977).

Provost, et al., "Lupus band test in untreated SLE patients: correlation of immunoglobulin desposition in the skin of the extensor forearm with clinical renal disease and serological abnormalities," *J Invest Dermatol.* 74(6):407–12 (1980).

Ravirajan, et al., "Antigen–binding diversity of human hybridoma autoantibodies derived from splenocytes of patients with SLE," *Lupus.* 1(3):157–65 (1992).

Raz, et al., "Cross–reactions of anti–DNA autoantibodies with cell surface proteins," *Eur J Immunol.* 23(2):383–90 (1993).

Reichlin Measurement of antibodies to Sm and uRNP by ELISA: clinical and serological correlations. In Mixed Connective Tissue Disease and Anti–Nuclear Antibodies. Kasukawa and Sharp, ed. (Excerpta medica, Elsevier Science Pub., Amsterdam (1987) pp. 85–96).

Reichlin & Mattioli, "Correlation of a precipitin reaction to an RNAprotein antigen and a low prevalence of nephritis in patients with systemic lupus erythematosus," *N Engl J Med.* 286(17):908–11 (1972).

Reichlin, et al., "Autoantibodies to the URNP particles: relationship to clinical diagnosis and nephritis," *Clin Exp Immunol.* 83(2):286–90 (1991).

Reichlin, et al., "Lupus autoantibodies to native DNA cross–react with the A and D SnRNP polypeptides," *J Clin Invest.* 93(1):443–9 (1994).

Rupin, et al., "Complete saturation of protamine sulphate by dsDNA is necessary in order to obtain a highly sensitive and specific anti–dsDNA ELISA," *J Immunol Methods.* 160(2):245–52 (1993).

Schur & Sandson, "Immunologic Factors and Clinical Activity in Systemic Lupus Erythematosus," *N. Engl. J. Med.*, 278:533–538 (1982).

Sharp, et al., "Mixed connective tissue disease—an apparently distinct rheumatic disease syndrome associated with a specific antibody to an extractable nuclear antigen (ENA)," *Am J Med.* 52(2):148–59 (1972).

Shoenfeld & Isenberg, "DNA antibody idiotypes: a review of their genetic, clinical, and immunopathologic features," *Semin Arthritis Rheum.* 16(4):245–52 (1987).

Sikorska, "Anti–thyroglobulin anti–idiotypic antibodies in sera of patients with Hashimoto's thyroiditis and Graves' disease," *J Immunol.* 137(12):3786–95 (1986).

Silvestris, et al., "Studies of anti–F(ab')2 antibodies and possible immunologic control mechanisms in systemic lupus erythematosus," *Arthritis Rheum.* 27(12):1387–96 (1984).

Sultan, "Recovery form anti–VIII:C (antihemophilic factor) autoimmune disease is dependent on generation of antiidiotypes against anti–VIII:C autoantibodies," *Proc. Natl. Acad. Sci. USA* 84:838–831 (1987).

Talal, et al., "Immunologic regulation of spontaneous antibodies to DNA and RNA I. Significance of IgM and IgG antibodies in SLE patients and asymptomatic relatives," *Clin Exp Immunol.* 25(3):377–82 (1976).

Tan & Kunkel, "Characteristics of a soluble nuclear antigen precipitating with SEAR of patients with Systemic Lupus Erythematosus," *J. Immunol.* 99:464–471 (1966).

Tan, et al., "Characteristics of a soluble nuclear antigen precipitating with SEAR of patients with systemic lupus erythematosus," *J. Clin. Invest.* 45:1732–1740 (1966).

Ter Borg, et al., "Changes in levels of antibodies against the 70 kDa and a polypeptides of the U1RNP complex in relation to exacerbations of systemic lupus erythematosus," *J. Rheumatol.* 18(3):363–7 (1991).

Tsao, et al., "Structural characteristics of the variable regions of immunoglobulin genes encoding a pathogenic autoantibody in murine lupus," *J Clin Invest.* 85(2):530–40 (1990).

Vlahakos, et al., "Murine monoclonal anti–DNA antibodies penetrate cells, bind to nuclei, and induce glomerular proliferation and proteinuria in vivo," *J Am Soc Nephrol.* 2(8):1345–54 (1992).

Wasicek & Reichlin, "Clinical and serological differences between systemic lupus erythematosus patients with antibodies to Ro versus patients with antibodies to Ro and La," J Clin Invest. 69(4):835–43 (1982).

Winfield, et al., "Specific concentration of polynucleotide immune complexes in the cryoprecipitates of patients with systemic lupus erythematosus," *J Clin Invest.* 56(3):563–70 (1975).

Winkler, et al., "IgG human monoclonal anti–DNA autoantibodies from patients with systemic lupus erythematosus," *Clin Exp Immunol.* 85(3):379–85 (1991).

Yamagata, et al., "Molecular properties of the Ro/SSA antigen and enzyme–linked immunosorbent assay for quantitation of antibody," *J Clin Invest.* 74(2):625–33 (1984).

* cited by examiner

ASSAY FOR PATHOGENICITY OF ANTI-DNA ANTIBODIES

This is a continuation of U.S. Ser. No. 08/450,188, filed May 25, 1995, now abandoned which is a continutation in part of U.S. Ser. No. 08/249,387, entitled "Assay for Pathogenecity of anti-DNA Antibodies" filed May 25, 1994, by Morris Reichlin and Eugen Koren, issued Oct. 28, 1997, as U.S. Pat. No. 5,681,700.

BACKGROUND OF THE INVENTION

The laboratory directed by Morris Reichlin at the Oklahoma Medical Research Foundation, Oklahoma City, Ok., has been engaged in the study of autoimmune responses to RNAprotein antigens in SLE patients for over 20 years. Researchers have reported the initial descriptions of the Ro/SSA (Clark, G. M., Reichlin, M. and Tomasi, T. B. *J. Immunol.*, 102:117–122 (1969)), La/SSB (Mattioli, M. and Reichlin, M. *Arthritis Rheum.*, 17:421–429 (1974)), and nRNP($U_1$RNP) 2. (Mattioli, M. and Reichlin, M. *J. Immunol.*, 107:1281–1290 (1971)) systems, while others described the Sm antigen (Tan, E. M. and Kunkel, H. G. *J. Immunol.*, 99:464–471 (1966)).

Over time, it has become apparent that certain profiles of anti-RNA protein antibodies are positively correlated with nephritis while other profiles are "negatively" correlated or "protected" from the development of serious renal disease. Thus, antibodies to nRNP($U_1$RNP) alone were found to have a low frequency of nephritis (Sharp, G. C., et al. *Am. J. Med.*, 52:148–159 (1972); Reichlin, M. and Mattioli, M. *N. Engl. J. Med.*, 286:908–911 (1972)) while patients with both anti-nRNP and anti-Sm (or anti-Sm alone) had a high frequency of nephritis (Reichlin, M. and Mattioli, M. *N. Engl. J. Med.*, 286:908–911 (1972); Maddison, P. J., et al. *J. Rheumatol.*, 5:407–411 (1978)). In patients with anti-Ro/SSA alone, a high frequency of nephritis was noted (Wasicek, C. A. and Reichlin, M. *J. Clin. Invest.*, 69:835–843 (1982); Hamilton, R. G., et al., *Arthritis Rheum.*, 31:496–505 (1988); Harley, J. B., et al. *Arthritis Rheum.*, 32(7):826–836 (1989)), while in those with both anti-Ro/SSA and anti-La/SSB, a low prevalence of nephritis was found. Studies of acid eluates from lupus nephritis kidneys have demonstrated enrichment of anti-Ro/SSA compared to serum levels (Maddison, P. J. and Reichlin, M. *Arthritis Rheum.*, 22:858–863 (1979)), supporting the participation of Ro/SSA-anti-Ro/SSA complexes in the development and/or the perpetuation of the nephritis. Elution studies of antibodies to the $U_1$RNP/Sm complex also showed enrichment, but the precise specificities of these complexes (anti-Sm or anti-nRNP) were not determined because of technical limitations (Koffler, et al. *J. Exp. Med.*, 134:294–312 (1971)). Serum levels of anti-Sm antibodies have been shown to fluctuate with disease activity (including nephritis) in some SLE patients (Barada, et al., *Arthritis Rheum.*, 24:1236–1244 (1981)). These data indicate a role for the Ro/SSA and Sm systems in the development of nephritis, but only 50% of patients with either anti-Ro/SSA alone or anti-nRNP and anti-Sm (or anti-Sm alone) develop nephritis.

Much data support a major role for the DNA-anti-DNA system in the pathogenesis of lupus nephritis Clinical studies show that high serum anti-DNA levels correlate positively with the activity of nephritis, and that remissions are associated with declining anti-DNA levels (Harley, et al., *Arthritis Rheum.* (1989); Tan, et al. *J. Clin. Invest.*, 45:1732–1740 (1966); Schur, P. H. and Sandson, J. *N. Engl. J. Med.*, 278:533–538 (1982)). Anti-DNA has been shown to be enriched in serum cryoglobulins (Winfield, et al., *J. Clin. Invest.*, 56:563–570 (1975)) and in acid eluates of lupus nephritis kidneys (Maddison and Reichlin (1979); Miniter, et al., *Arthritis Rheum.*, 22:959–968 (1979); Beaulieu, et al. *Arthritis Rheum.*, 22:565–570 (1979)). In all these studies, the specificity of these antibodies are to dsDNA (double stranded or native DNA).

Antibodies to native or ds DNA play a special role in the clinical diagnosis and pathology of Systemic Lupus Erythematosus (SLE). These 19, autoantibodies are highly specific, frequently correlate positively with disease activity (especially nephritis), and remissions are usually associated with declining anti-dsDNA levels (Hahn and Tsao, Antibodies to DNA. -Tn Dubois, Systemic Lupus Erythematosus. D-J. Wallace and B. H. Hahn, editors. (Lea and Febiger, Philadelphia, Pa. 1993) pp. 195–201; Harley, et al., *Arthritis Rheum.* 32:826–836 (1989); Tan, et al., *J. Clin. Invest.* 45:1732–1740 (1966); Schur and Sandson, *N. Engl. T. Med.* 278:533–538 (1982)). Patients who produce antibodies to the Ro/SSA and La/SSB (Harley, et al. (1989); Wasicek and Reichlin, *J. Clin. Invest.* 69:835–843 (1982); Hamilton, et al., *Arthritis Rheum.* 31:496–505 (1988); antigens as well as those that only have precipitins to $U_1$RNP (Sharp, Am. J. Med. 52:148–159 (1972); Reichlin and Mattioli, *N. Engl. J. Med.* 86:908–911 (1972)) very infrequently have anti-dsDNA in their serum and have a correspondingly low prevalence of nephritis. The mechanisms of these negative relationships of antibodies to Ro/SSA and La/SSB and $U_1$RNP with anti-dsDNA are not understood.

Studies have been reported in the literature describing differences in the ability of murine monoclonal antibodies to dsDNA to induce nephritis when hybridomas producing these antibodies are placed in normal mice (Tsao, et al. *J. Clin. Invest.*, 85:530–540 (1990)). Others have shown that murine monoclonal antibodies penetrate cells, bind to nuclei, and induce glomerular proliferation and proteinuria in vivo (Vlahakos, et al., *J. Am. Soc. Nephrol.* 2:1345–1354 (1992)). Most recently, others have reported direct in vitro binding of murine monoclonal antibodies to glomeruli which is DNA dependent (DiValerio, et al., *Clin. Res.*, 42:139A (1994)).

However, many questions remain about the mechanisms of lupus nephritis and especially the correlations that can be drawn from samples of the most accessible body fluid, the plasma. First, as many as 30% of lupus nephritis patients have never had measurable antibodies to dsDNA in their plasma. Second, as many as 25% of lupus patients with anti-dsDNA in their plasma do not develop nephritis even after many years. It is conceivable that in the first group of patients that anti-dsDNA is never detected in the plasma, because it is immediately complexed with antigen and deposited in the kidney and elsewhere. No one has studied the kidneys of such patients to see if there are large renal deposits composed of DNA and anti-DNA Some anti-DNA populations may not be nephritogenic because: (1) of poor complement fixing capacity (Miniter, et al., (1979) or Beaulieu (1979)), or (2) because they are largely IgM in nature (Pennebaker, et al. *J. Clin. Invest.*, 60:1331–1338 (1977); Provost, et al., *J. Invest. Dermatol.*, 74:407–412 (1980); Talal, et al., Clin. Exp. Immunol., 25:377–382 (1976)). These two latter observations may not be mutually exclusive, but systematic studies to assess their independent contributions when both are present have not been done. Other molecular factors that have been correlated with "pathogenicity" include high avidity, IgG isotype, high cationic charge, ability to precipitate with DNA, direct binding to glomeruli in vitro, and ability to bind DNA planted in glomerular structures. Thus, the presence of anti-DNA does not always lead to nephritis nor does its consistent absence in the plasma assure protection from serious nephritis. It may well be that lupus nephritis can develop in the absence of antibodies to dsDNA. What is clearly lacking in available diagnostic armamentarium is the ability to distinguish "pathogenic" from non-pathogenic antibodies. There are no simple "tests" at present that can distinguish "bad" from "good" or "harmless" anti-dsDNA antibodies.

It is therefore an object of the present invention to provide methods and reagents for assessment of pathogenicity of antibodies to double stranded (ds) DNA.

It is another object of the present invention to develop specific therapy based on anti-idiotypes to anti-dsDNA.

SUMMARY OF THE INVENTION

Based on the interpretations of observations regarding a correlation in lupus patient sera between the presence of certain autoantibodies and the lack of, or presence of, nephritis and severity of pathology, assays and treatments have been developed for lupus patients predisposed to nephritis The initial observations are that the cross reaction of anti-dsDNA antibodies with denatured A and D SnRNP proteins as they exist in Western blot is a marker for pathogenicity of anti-dsDNA in culture. It also supports the hypothesis that the A and D SnRNP protein may be the original immunogenic stimulus leading to the production of anti-dsDNA. These anti-dsDNA antibodies cross reactive with A and D proteins are also unusual in that they are able to penetrate living cells, leading to cell injury and death, which forms further support for the antibodies in patients being responsible for cell death and injury, especially nephritis. The second set of observations is that the presence of certain other autoantibodies, anti-La/SSB, anti-Ro/SSA or anti-$U_1$RNP, that are cross reactive with the anti-dsDNA antibodies, protect against cell damage and death. Accordingly, patients characterized by the presence of either anti-La/SSB or anti-$U_1$RNP antibodies that are cross reactive with the anti-dsDNA do not get as sick and rarely develop kidney disease.

Using these observations, assays that are 2Q- prognostic for patients that will develop nephritis have been developed where patient serum is screened, preferably by Western blot, for the presence of anti-dsDNA antibodies that are cross reactive with A and D SnRNP proteins. Other immunoassays are also described. The assays are based on the use of either peptides containing epitopes (defined as four to seven amino acids forming a structure bound by the variable region of an antibody) of the A and D SnRNP proteins bound by the anti-dsDNA antibodies, or the entire A and D SnRNP proteins.

Therapeutic compositions have also been developed using either antibodies that block the pathogenicity of the anti-dsDNA antibodies, such as the naturally occurring anti-La/SSB and the anti-$U_1$RNP antibodies that are cross reactive with the anti-dsDNA or using the antigenic peptides or the whole A and D proteins to induce tolerance.

DETAILED DESCRIPTION OF THE INVENTION

Figure 1A:
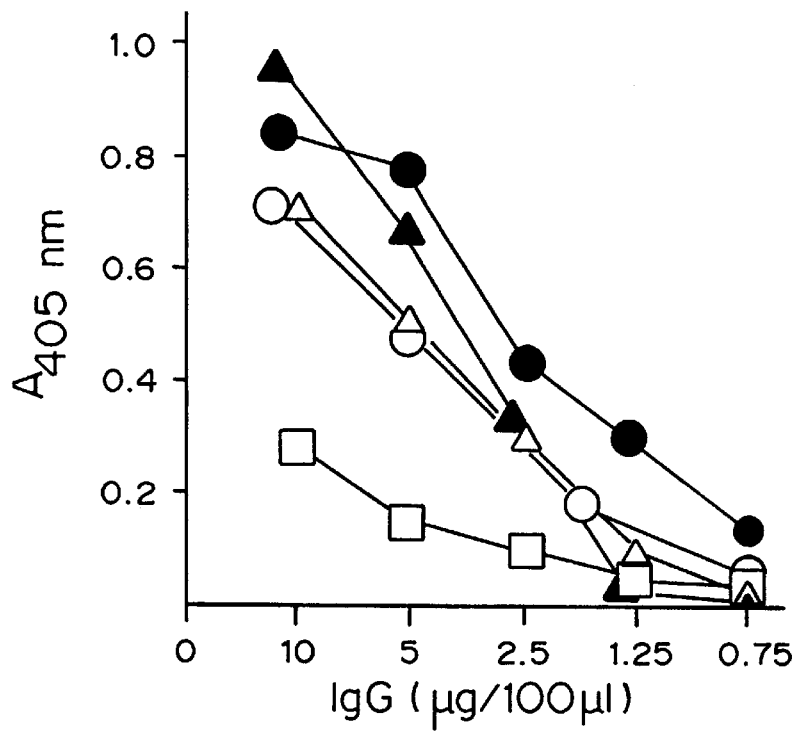
FIGS. 1a and 1b are graphs showing: (a) Patients No. 1 (●) with anti-Ro/SSA and No. 2 (▲), 3 (▲) and 4 (○) with anti-La/SSB, and a normal control serum (□) were separately isolated with dsDNA affinity column. Their isolated IgG anti-dsDNA activities were titrated on dsDNA-coated plates. (b) Inhibition of the reaction of sera No. 1 (●), 2 (▲), 3 (▲), and 4 (○), IgG anti-dsDNA activity by dsDNA. IgG anti-dsDNA concentration is 5 gg/100 ul in each case.

Work is presented which defines a new molecular correlate of anti-dsDNA with a newly discovered cross reaction to two proteins identified as the A and D SnRNP proteins. A prognostic assay based on this cross reaction correlates closely with the pathogenic potential of anti-dsDNA to injure many cell types in tissue culture and also correlates clinically with organ damage; i.e., nephritis. Populations of autoantibodies to the transcription termination factor La/SSB and the splicing factor $U_1$RNP act as antibodies to anti-dsDNA through the idiotype network. These anti-idiotypes can be used to down regulate anti-dsDNA immunologically specific therapy in patients who have active SLE associated with anti-dsDNA.

The data in the examples implicate a previously unrecognized cross reaction of anti-dsDNA with the denatured A and D SnRNP proteins as they exist in Western blot as a marker for pathogenicity of anti-dsDNA for cells in culture. Experiments on cells in tissue culture demonstrate in vitro effects of antibodies to dsDNA which may reflect their in vivo pathogenicity. Since the preliminary results of Example 1 were published in January 1994, several additional discoveries not only expand the original findings, but also provide direction for the development of an approach to define the pathogenic potential of anti-dsDNA, as well as a specific method for turning off the anti-dsDNA response; in effect a directed form of immunotherapy that should be much more specific and safer than current methods of immunosuppression.

Description of Biochemistry and Immunochemistry of $U_1$RNP and Sm Particles

Understanding of the immune responses to the $U_1$RNP and Sm particles has increased as the biochemistry of these particles has been elucidated.

The U (uridine rich) particles are composed of a single RNA complexed noncovalently with five common and between one and three unique polypeptides Antibodies to $U_1$RNP are directed to-the unique polypeptides designated 68 kDa (or 70 kDA), A (34 kDa) and C (19 kDa). There are five other common proteins ranging in size from 28 to 12 kDa. Antibodies to Sm are directed to three of the common polypeptides designated B (28 kDa), B' (26 kDa) and D (16 kDa).

Thus, anti-nRNP or anti-$U_1$RNP is largely directed to the $U_1$ specific polypeptides of 68 (70), 34 (A) and 19 (C) kDa while anti-Sm is directed to a doublet of 28 10 and 26 kDa (BB') which are closely related, and D, which are found in all the U particles and define the anti-Sm specificity.

As a result, the A protein is a key target for the anti-$U_1$RNP specificity and the D protein a major target for the anti-Sm specificity. The shared antigenicity of the A and D SnRNP proteins was reported by Reichlin, et al., *J. Clin. Invest.*, 93:443–449 (January 1994)).

As has been reported, immune responses to $U_1RNP$ alone are associated with a low prevalence of nephritis while a response directed to Sm alone or in combination with $U_1RNP$ is associated with a high risk of nephritis (Sharp, et al., (1972); Reichlin and Mattioli (1972); Maddison, et al., (1978)). In the data in the following examples, antibodies to A and D, whether IgG or IgM, are shown to be closely linked with anti-dsDNA. These apparently antigenically unique and structurally non-homologous A and D proteins share an epitope(s) which is the basis for the cross reaction with antibodies to dsDNA. Neither of these phenomena has been previously reported.

These findings lead to an alternate picture of antibodies to dsDNA from several points of view. The presence of this cross reaction of the denatured A and D proteins with anti-dsDNA provides multiple reinforcing stimuli to promote the production of both anti-dsDNA and anti-SnRNP antibodies. They raise the possibility that the A and D proteins might be the original immunogenic stimulus that leads to the production of anti-dsDNA. Finally, the anti-dsDNA antibodies that cross react with the A and D proteins penetrate living cells in culture leading to their injury. This may have relevance to their role in in vivo pathogenesis and can serve as a marker for pathogenic antibodies to dsDNA.

Assays for Diagnosis and Prognosis and Reagents As described in Examples 1, 5, 6 and 8, the presence in a patient serum of anti-dsDNA which is immunoreactive with A and D SnRNP is predictive of severity of disease and probability of developing nephritis, if the patient does not also have anti-La/SSB and/or anti-$U_1RNP$ which is immunoreactive with the anti-dsDNA.

Peptide-based assay for anti-dsDNA An immunoassay utilizing a peptide cross-reactive with anti-dsDNA is both diagnostic and provides information about pathogenicity.

Identification of peptides is described below in Example 8. Isolation of A and D proteins to which the anti-dsDNA binds is described below. The key feature is that the peptides are immunoreactive with the anti-dsDNA that binds both the A and D SnRNP proteins. The peptides can be made synthetically using standard peptide synthesis, by isolation and enzymatic cleavage of naturally occurring protein and routine screening of fragments by binding to a column having anti-dsDNA antibody coupled thereto, or by expression of all or a part of the gene encoding the A or D SnRNP encoding an epitope present in both proteins bound by the anti-dsDNA.

The immunoassay can be performed in the same way as described in the examples, using Western blots, or immunoprecipitation of patient sera with native or recombinant proteins A and D, in cell extracts or purified form. A number of immunoassays are known to those skilled in the art, where the variables are only whether antigen or antibody is added in the sample or is immobilized to an inert substrate, labeled or detected using an enzyme-substrate or chromagen detection means.

Cell-based assay for anti-dsDNA An assay using patient sera can also be examined using cell culture studies to screen for autoantibodies which penetrate cell nuclei, as described, for example, in Example 5.

Assay for pathogenicity and nephritis As described above for detection of anti-dsDNA, one can also screen for the presence of anti-La/SSE antibodies or anti-$U_1RNP$ that cross react with the anti-dsDNA, which would be predictive of less severe disease and a lower probability of developing nephritis. Screening initially for the anti-La/SSB or anti-$U_1RNP$ is done using either purified La/SSB or $U_1RNP$, prepared as described below.

1. Affinity Isolation of $U_1RNP$ and La/SSB.

These methods are based on selection of appropriate human sera, isolation of IgG from these sera, coupling to cyanogen bromide activated Sepharose™, application of tissue extracts (calf thymus and/or human tissue culture cells; e.g., HeLa or Molt-4) and elution of antigenically active materials with 3.5 M $MgCl_2$.

For the preparation of anti-$U_1RNP$ columns a plasma is selected which gives a single precipitin line with calf thymus extract, immunoprecipitates only $U_1RNP$, and does not react with purified Sm antigen in ELISA. IgG is isolated by passing plasma equilibrated at 0.02 M NaCl, pH 7.2, Tris buffered saline (TBS), over a DE52 (Whatman) column equilibrated with the same buffer. IgG passes directly through this column and is only IgG when examined by immunoelectrophoresis. IgG is coupled to Sepharose™ via cyanogen bromide activation according to the manufacturer's instructions. One hundred grams calf thymus tissue is homogenized in a Waring Blender with 3 volumes cold TBS at 4° C. The extract is centrifuged at 18,000 rpm in a Sorval centrifuge for 60 minutes and salt added to the supernatant to a final concentration of 0.5 M NaCl. This extract is then passed over the IgG Sepharose™ Tm-anti-$U_1RNP$ column and washed with TBS adjusted to 0.5 M NaCl until the O.D. is less than 0.05 at 280 nM. Protein is eluted with 3.5 M $MgCl_2$. The $U_1RNP$ is concentrated to a protein concentration of 5.0 mg/ml (Bio-Rad), dialyzed against $TBS_1$ and stored at 70° C. This material is active $U_1RNP$ by precipitation in agar gel diffusion and for coating plates for quantitative ELISA. It contains all the recognized $U_1RNP$ peptides in Western blot: 70 kD, A, BB', C and D.

La/SSB is similarly prepared from calf thymus extract but IgG is prepared from a serum with an anti-La/SSB precipitin. Since all anti-La/SSB sera contain anti-Ro/SSA, extracts are first passed over an IgG anti-Ro/SSA column to remove Ro/SSA antigen. Other operations are the same as for the preparation of $U_1RNP$. La/SSB prepared in this way can be shown to be free of Ro/SSA, $U_1RNP$ or Sm by Western immunoblotting.

2. Preparation of A and D Proteins from Human $U_1RNP$ Prepared from HeLa Cells

Purification of $U_1RNP$: Hela cells ($2 \times 10^8$) are collected by centrifugation, washed with 0.02 M TBS, sonicated in ml of 0.05 M Tris, 0.3 M NaCl, 0.05% NP-40, 0.001 M $MgCl_2$ at 0° C. for 3 periods of 20 s, and centrifuged at 10,000 g for 60 min at 4° C. The supernatant is passed through the anti-$U_1RNP$ affinity column. The column is washed with 0.02 M TBS and $U_1RNP$ is eluted with 3.5 M $MgCl_2$. The eluate is then dialyzed against 0.02 M TBS and stored at −70° C.

SDS PAGE and elution of A and D: The purified $U_1RNP$ is separated into polypeptides by SDS-PAGE using 3 mm×180 mm×200 mm 12% gel. Strips from both sides of the gel are then cut and stained by 0.32% Coomassie blue R-250 (Bio-Rad). The remainder of the gel is stored at −70° C. The section of the gel containing the A and D polypeptide is identified according to the stained gel strips and isolated. The A and D polypeptides are electroeluted from each section of the gel using the Electroeluter™ (Bio-Rad, Model 422) concentrated by Centricon-10™ (Amicon Division, W. R. Grace & Co.), and stored at -70° C. Recombinant A and D proteins are prepared by standard methods once the appropriate cDNAs are inserted into appropriate expression vectors.

Therapeutic Applicants and Pharmaceutical Compositions Based on the results in Examples 1 to 6, one can prepare anti-Id reagents (for anti-dsDNA) that can be used to downregulate the production of anti-dsDNA described in Example 7.

In one embodiment, the free peptide or a conjugate of this peptide can be used in tolerance induction which could ablate anti-dsDNA.

In a second embodiment, reagents that are antibodies to anti-dsDNA (i.e., anti-La/SSB, anti-Ro/SSA or anti-$U_1$RNP) could be used to down regulate anti-dsDNA production of SLE patients.

Peptide or Protein-based Compositions

Attempts to influence anti-DNA production in mouse lupus in vivo or in human lymphocytes in vitro, are described by Borel, et al., *Science*, 182:76–77 (1973); Borel, et al., *J. Clin. Invest.*, 61:276–286 (1978); Borel, Y. and Borel, H., *J. Clin. Invest.*, 82:1901–1907 (1988). As described by Borel, et al., oligonucleotides or nucleosides are attached to isologous (same species) IgG and this is allegedly effective in (1) inhibiting the development of an immune response to DNA in murine lupus and decreasing disease severity, and (2) inhibiting human cells from producing anti-DNA in vitro. The "DNA" used here is single stranded or denatured which is not optimal since the most important response in SLE is to native 2:=. or double stranded DNA. Borel's work provides an appropriate "carrier" for the toleragen, isologous gamma globulin.

As described herein, peptide(s) that are immunoreactive with dsDNA and are derived from the A and D proteins can be used to induce tolerance in a patient. Antibodies to dsDNA are the disease specific pathogenic autoantibodies of the greatest interest. There are two major possibilities: (1) inject free peptide, or (2) inject peptide-coupled to human IgG, for example, coupled using glutaraldehyde or carbodiimide. These two approaches should both induce T cell tolerance- They may also be effective in inducing B cell tolerance. Both approaches are attractive since there is little chance of "boosting" the anti-dsDNA response. Should the latter occur, it can be treated by standard immunosuppressive drugs, alone or in combination with anti-La/SSB or-anti-$U_1$RNP, as described below Behavior of the peptide or peptide conjugate is first studied in an appropriate animal model in order to determine efficacy and optimal dosages.

There are several that could be used, but the most attractive is the Palmerston North Mouse. It has been shown that these mice, which all produce anti-dsDNA and develop nephritis, also develop anti-$U_1$RNP and Sm responses in almost all the animals with a dominant immune response against the A protein of $U_1$RNP measured in Western blot, as reported by Handwerger, et al., *Clin. Res.* 42:315A (1994). These mice have no detectable antibodies in the first three months of life but rapidly develop them after six months of age and experience a fulminant glomerulonephritis associated with anti-dsDNA antibodies. Dosage would range from 3 to 300 micrograms per mouse given weekly 20-- in the first experiments.

The same result obtained by administering peptide or a peptide conjugate can be achieved by coupling recombinant A or D protein to human IgG.

Anti-La/SSB, Anti-Ro/SSA and Anti-$U_1$RNP Antibodies That Are Cross Reactive With Anti-dsDNA Antibodies The reactivity of isolated anti-La/SSB, anti-Ro/SSA and anti-$U_1$RNP with anti-dsDNA from various patients as well as the antibodies unmasked by absorption with La/SSB, Ro/SSA and $U_1$RNP from individual patients with anti-A and D reactivity, and the public or private nature of these reactivities, can be determined using standard methodology, as described in more detail in Examples 6–9.

Issues in this regard include the pattern of reactivity of anti-La/SSB, anti-Ro/SSA or anti-$U_1$RNP isolated from an individual patient In addition to the unmasked anti-A and D from the same patient, specific affinity purified antibodies including (1) unmasked anti-A and D from the same patient, (2) unmasked anti-A and D antibodies from other patients' sera absorbed with La/SSB, (3) unmasked anti-A and D antibodies from other patients' sera absorbed with $U_1$RNP, and (4) affinity purified anti-dsDNA antibodies which cross react with the SnRNP A and D proteins in Western blot, can be used to characterize the anti-La/SSB, anti-$U_1$RNP, and anti-dsDNA antibodies.

The isolated anti-La/SSB (or anti-$U_1$RNP) is pepsin digested, then used to coat Immulon™ plates.

The isolated affinity purified unmasked antibodies and anti-dsDNA antibodies, all of which are IgG, can then be assayed for their reactivity with the anti-La/SSB $Fab_2$. Binding is assessed by reactivity with a conjugate of goat anti-human gamma chain specific alkaline phosphatase conjugate. Color is developed with the addition of the substrate para-nitrophenyl phosphate at 405 nm on a Multitek™ scanner.

Specificity is assured by the ability of free La/SSB antigen to block the reactivity of anti-La/SSB with unmasked anti-A and D or anti-dsDNA. Similarly, $U_1$RNP should block the reactivity of anti-$U_1$RNP with unmasked anti-A and D or anti-dsDNA.

Experiments such as these are used to define the sharing or cross reactivity on the one hand, or the individual specificity of these antibodies on the other, in these idiotype network relationships.

Patients having broadly cross reactive antibodies can be plasmapheresed and used as donors for immunotherapy for patients whose anti-dsDNA is reactive with the donor's anti-La/SSB or anti-UIRNP. This then becomes as simple as intravenous plasma therapy.

An alternative approach is to screen recombinant libraries of Ig variable ("V") regions made from cDNA's reverse transcribed from mRNA extracted from peripheral blood lymphocytes from patients who produce anti-La/SSB and/or anti-$U_1$RNP. A number of such libraries can be constructed and then screened for clones reactive with Fab anti-dsDNA but not normal Fab. These can then be used to produce any desired amount of anti-idiotype to anti-dsDNA. Alternatively, murine recombinant monoclonal anti-idiotypic antibodies directed against relevant idiotope(s) on anti-dsDNA can be produced.

This can be accomplished by the use of Pharmacia's (Pharmacia LKB Biotechnology, Sweden) "Recombinant Phage Antibody System" (RPAS), which generates a single-chain Fv fragment (ScFv) that incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans. The murine ScFv molecules can be "humanized" to further reduce the immunogenic stimulus presented.

Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes.

These "humanized" antibodies present a lesser xenograft rejection stimulus when introduced to a human recipient.

To accomplish humanization of a selected mouse monoclonal antibody, the CDR grafting method described by Daugherty, et al., Nucl. Acids Res., 19:2471–2476, 1991, incorporated herein by reference, can be used. Briefly, the variable region DNA of a selected animal recombinant anti-idiotypic ScFv is sequenced by the method of Clackson, T., et al., Nature, 352:624–688, 1991, incorporated herein by reference. Using this sequence, animal CDRs are distinguished from animal framework regions (FR) based on locations of the CDRs in known sequences of animal variable genes. Kabat, H. A., et al.l, Sequences of Proteins of Immunological Interest, 4th Ed. (U.S. Dept. health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CRDs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The present invention will be further understood by reference to the following examples.

Example 1: Evidence That Antibodies to dsDNA Cross React With the A and D SnRNP Proteins.

Fifty-four patients' sera containing anti-nDNA were from SLE patients who satisfied American College of Rheumatology revised criteria for the classification of SLE. 113 sera were obtained from patients without anti-nDNA and were from several groups. Twenty patients without precipitins all satisfied ARA criteria for SLE. Forty-nine sera were from patients with either anti-Ro/SSA precipitins or with both anti-Ro/SSA and anti-La/SSB and having either SLE, subacute cutaneous lupus erythematosus or Sjögren's syndrome. Thirty-four patients with anti-U$_1$RNP precipitins had either SLE, scleroderma, polymyositis or, in a few instances, an overlap of two of these diseases. Multiple samples were obtained on most patients and were immunologically characterized.

Anti-nDNA was measured by the crithidia assay, Aarden, et al., Ann. NY Acad. Sci. 254:505–515 (1975). Precipitating antibodies to Ro/SSA, La/SSB, U$_1$RNP, and Sm were assayed by gel diffusion using bovine spleen or calf thymus extracts, using the methods of Clark, et al., J. Immunol. 102:117–120 (1969); Mattioli and Reichlin, Arthritis Rheu. 17:421–429 (1974). Inhibition of Western blot reactivity against the A and D proteins is accomplished by preincubating appropriate dilutions of the human sera for 1 h at room temperature with calf thymus DNA, Sigma Chemical Co., St. Louis, Mo., at a final concentration of 50 μg/ml. DNA concentrations are assessed by optical density at 260 nm using an extinction value of 1.0 at 50 μg/ml. Solid phase assays for anti-U$_1$RNP and anti-Sm, as well as affinity purification of U$_1$RNP and Sm. were performed as described by Reichlin "Measurement of antibodies to Sm and uRNP by ELISA: clinical and serological correlations. In Mixed Connective Tissue Disease and Anti-Nuclear Antibodies. Kasukawa and Sharp, ed. (Excerpta medica, Elsevier Science Pub., Amsterdam (1987) pp. 85–96).

Antibodies to nDNA were purified with DNA cellulose which contains double-stranded DNA, Sigma Chemical Co., St. Louis, Mo. The DNA cellulose was equilibrated with a buffer containing 0.02 M Tris 0.145 M NaCl, pH 7.2. Sera were dialyzed against this buffer and then applied to the column. Effluents were collected until the OD at 280 nm fell below 0.01 and then reconstituted to the original serum volume by concentration by the Centriprepm method, Amicon Corp., Danvers, Ma. Specific antibody was eluted with 3 M MgCl$_2$, dialyzed against the Tris-NaCl buffer, and assayed for anti-nDNA by the Crithidia assay. These eluates were also concentrated to the volume of the serum from which they were prepared. Gamma globulin concentration was measured using an OD value of 1.5/mg protein at 280 nm.

SLE sera containing anti-dsDNA (40 of 54 or 74.1%) bound two proteins of 34 and 16 kD in Molt-4 extract, the size of the SnRNP A and D protein. It was hypothesized that these were the A and D SnRNP proteins because reactivity with these bands was depleted from anti-dsDNA sera by DNA cellulose columns. Only 9 of 113 SLE sera without dsDNA bound these two proteins in Western blot. Antibodies to dsDNA correlated closely with anti-A and D in 7 of 8 patients followed sequentially, r=0.7865. Of nine human polyclonal anti-dsDNA isolated from DNA cellulose columns, seven reacted equally with A and D, and two reacted predominantly with D. Two of three murine monoclonal anti-dsDNA antibodies isolated from NZB/NZW F$_1$ hybrid mice bound A and D equally in Western blot with a titer greater than 1/40,000.

Example 2: There is an IgM Counterpart of the IgG Anti-dsDNA with Cross Reactivity with the SnRNP A and D Proteins As described below, it has now been shown that IgM anti-A and D proteins, but not IgG anti-A and D proteins, are a common finding in sera with anti-Ro/SSA, or both anti-Ro/SSA and anti-La/SSB precipitins, as well as lupus sera without any precipitins, as shown in Table 1. These three groups total 183 sera and exclude sera with anti-Sm and/or iF anti-UIRNP precipitins.

TABLE 1

Prevalence of Sera with only IgM anti-A and D Protein Antibodies in Western blot.

| Disease and/or Precipitin | Number | IgM Positive Only |
|---|---|---|
| Anti-Ro/SSA (SLE, SCLE, SS) | 110 | 29 |
| Anti-Ro and anti-La (SLE, SCLE, SS) | 32 | 7 |
| SLE (anti-Sm) | 12 | 0 |
| SLE (anti-Sm/nRNP) | 18 | 0 |
| SLE or overlap (anti-nRNP) | 34 | 0 |
| SLE (no precipitins) | 41 | 12 |

Note that 47 of 183 sera in the three groups mentioned above, or 25.7%, have IgM anti-A and D without IgG anti-A and D. Interestingly, none of 64 sera with anti-Sm and/or anti-U$_1$RNP precipitins had only IgM anti-A and D, although more than 90% of the anti-Sm sera had IgG anti-A and D, as did 20% of the anti-U$_1$RNP sera. Thus, IgM anti-A and D is a common feature of SLE sera which lack anti-Sm or anti-U$_1$RNP precipitins. (X$^2$=19.6, p less than 0.000001, odds ratio greater than 1000). This statistic refers to the comparative prevalence of IgM anti-A and D in sera without anti-Sm or anti-U$_1$RNP precipitins to those with anti-Sm or anti-U$_1$RNP precipitins (n=64).

To assess the cross-reactivity of this IgM anti-A and D with anti-dsDNA, these sera were assayed in ELISA on dsDNA coated plates. The results are shown in Table 2.

TABLE 2

Relationship of Western Blot for IgM Anti-A and D with IgM Anti-dsDNA.

| Disease and/or Precipitin | Number | Anti-A and D, dsDNA | A and D | dsDNA |
| --- | --- | --- | --- | --- |
| Anti-Ro/SSA (SLE, SCLE, SS) | 110 | 20 | 9 | 0 |
| Anti-Ro and La (SLE, SCLE, SS) | 32 | 3 | 4 | 0 |
| SLE with No Precipitins | 41 | 7 | 5 | 1 |

As shown, 30 of the 48 sera with IgM anti-A and D also had IgM anti-dsDNA. Only one serum had IgM anti-dsDNA without IgM anti-A and D. This strengthens the relationship of IgM anti-A and D to IgM anti-dsDNA similar to what is described for the IgG anti-dsDNA and anti-A and D reactions. In addition, the IgM A and D reactions in Western blot can be blocked by addition of between 5 and 50 µg/ml of dsDNA, but not RNA, similarly to the IgG anti-A and D. Thus, there is a strong association of the IgM anti-dsDNA and anti-A and D reactivities. X$^2$ =100, odds ratio=201, p less than $10^{30}$.

The patients with IgM anti-dsDNA and IgM anti-A and D have milder disease and a very low prevalence of nephritis. The relationship of IgM and anti-dsDNA to milder disease has been long recognized. The significance of this finding is the demonstration that the relationship of the anti-dsDNA to the A and D cross reactivity extends the previous observations made with the IgG class to the IgM class.

Example 3: Human IgG Monoclonal Anti-dsDNA Cross React with SnRNP A and D Proteins The studies with mouse monoclonal anti-dsDNA antibodies and human polyclonal anti-dsDNA were confirmed with studies using human IgG monoclonal antibodies to dsDNA described by Winkler, et al., *Clin. Exp. Immunol.*, 85:379–385 (1991). At concentrations of 1 µg/ml these monoclonal antibodies all bind the SnRNP A and D proteins of Molt-4 extract in Western blot. This result eliminates any question about the specificity of the antibodies in a polyclonal autoimmune serum which are reacting with the A and D proteins in Western blot. In addition, there are numerous steps in the development of assays (i.e., the specificity of peptide sequences which serve as the epitope or antigenic determinant responsible for the cross reactivity of the SnRNP A and D proteins) which are optimally validated by reactivity with monoclonal antibodies. Monoclonal antibodies showing these dual specificities (anti-dsDNA on the one hand and anti-A and D on the other) will invariably be superior in fine specificity studies to polyclonal anti-dsDNA isolated from patients in that they represent a single specificity and the results will not be obscured by "dilution" with anti-dsDNA antibodies which lack this dual specificity.

Example 4: Validation of the Specificity of the Cross Reaction of Anti-dsDNA with the SnRNP A and D Proteins All of the original observations used a whole cell lysate of Molt-4 cells, a malignant T cell line, as the antigen source for the SnRNP A and D proteins.

The reactions with the cell lysate were validated with affinity purified U$_1$RNP as a source of A and D.

However, it is still possible that even this affinity purified material has other proteins of identical size with A and D which co-purify. Accordingly, two forms of recombinant D protein were obtained from Dr. Sally Hoch of the Agouron Institute in La Jolla, Calif., and a cDNA clone encoding the A protein was obtained from Dr. Jack Keene of Duke University and used to express recombinant A protein.

Several experiments with Sm D were performed which confirm in detail the original findings. Five of five SLE sera with anti-dsDNA that bind D in crude extracts strongly bind recombinant D (100%). Normal human sera do not bind recombinant D. The two mouse monoclonal anti-dsDNA, two human monoclonal anti-dsDNA, and one affinity purified anti-dsDNA antibody were tested and they all strongly bind recombinant D (100%). These same sera, eluates, and monoclonals with anti-dsDNA specificity were also tested with recombinant A and shown to bind. These results provide powerful evidence for the molecular nature of the two bands in Molt-4 of molecular weight 34 and 16 kD which support the identity of the proteins being the SnRNP A and D proteins.

Example 5: Pathogenic Effects of Murine and Human Anti-dsDNA on Cells in Culture Results have been obtained that show that both murine monoclonal and human polyclonal anti-dsDNA antibodies can bind to, penetrate, and injure cells in culture. Moreover, there is a correlation of the ability of the anti-dsDNA antibodies to bind A and D SnRNP proteins with the ability to mediate cell injury.

Studies were performed with three murine monoclonal antibodies: BWds1, BSds3 and 5GD5, whose reactivity with A and D was determined in Western blot. The first two monoclonals bind A and D while 5GD does not. The first two are pathogenic in mice while the third one is not. The pathogenic monoclonals have also been shown to bind and injure pig kidney epithelial cells in culture. One of these (BWd53) requires complement for its cytotoxic effect while the other (BWds1) does not fix complement but 20- penetrates the cell and eventually over a period of days injures the cells. The non-pathogenic monoclonal antibody 5GD which does not bind the A and D proteins does not bind the cells in culture.

Similar experiments were also performed with affinity purified polyclonal human anti-dsDNA and similar results obtained. Cross reaction with the A and D SnRNP proteins is associated with the ability to bind, penetrate and injure cells in culture.

Example 6: Antibodies to U$_1$RNP are Anti-Idiotypes to Anti-dsDNA

Experiments were designed to remove anti-U$_1$RNP from lupus sera which, before this removal, neither contained IgG anti-dsDNA antibody nor bound the SnRNP A and D proteins. Affinity purified U$_1$RNP was used to absorb appropriate sera containing antibodies to these RNA proteins. Sera were tested in Western blot and ELISAs for anti-dsDNA before and after absorption. With five anti-U$_1$RNP sera, the absorbed sera exhibited IgG antibody activity against the SnRNP A and D bands in Western blot against Molt-4 extract. In addition, antibody activity against dsDNA appeared after the absorption. Data from the U$_1$RNP absorbed sera are shown in Table 3.

TABLE 3

Antibody Activity to dsDNA After
Absorption of Anti-$U_1$RNP Sera by Affinity
Purified $U_1$RNP-Assay in ELISA for dsDNA.

| Human Serum No. | O.D.$_{410}$ After Absorption | O.D.$_{410}$ Before Absorption |
| --- | --- | --- |
| 195 | .495 | .170 |
| 817 | .695 | .437 |
| 1118 | .674 | .217 |
| 1137 | .740 | .294 |
| 1546 | .831 | .025 |
| Mean ± S.D. | .686 ± .125 | .299 ± .152 |

These results are interpreted to mean that anti-La/SSB and anti-UIRNP are anti-idiotypes (or anti-antibodies) to anti-dsDNA and removal of the anti-idiotype (anti-La/SSB or anti-$U_1$RNP) by antigen unmasks the idiotype; in this case anti-dsDNA.

Example 6: Antibodies to Ro/SSA and anti-La/SSB are Anti-Idiotypes to Anti-dsDNA The relationship of anti-Ro/SSA and antiLa/SSB antibodies to anti-dsDNA in sera from patients with systemic lupus erythematosus was determined as follows. Sera with anti-Ro/SSA alone or those with anti-La/SSB were absorbed with purified Ro/SSA and La/SSB, respectively. The absorbed sera were then tested for reactivity with Molt 4 extract in Western blot and dsDNA in ELISA. With selected sera, anti-dsDNA was isolated on DNA cellulose columns and anti-Ro/SSA to anti-La/SSB were isolated on antigen affinity columns. Reactivity between anti-dsDNA and autologous anti-Ro/SSA or anti-La/SSB was studied as well as inhibition by cognate antigens. Anti-Ro/SSA sera (5) and anti-Ro/SSA and anti-La/SSB sera (8) were absorbed with Ro/SSA and La/SSB, respectively. After absorption, all sera showed reactivity with SNRNP A and D bands in Western blot and some showed reactivity with dsDNA in ELISA. Anti-dsDNA populations (4) were purified on dsDNA cellulose columns. Anti-Ro/SSA (1) and anti-La/SSB (3) were affinity-purified from the same sera as the anti-dsDNA. In all cases, anti-dsDNA bound autologous anti-Ro/SSA and anti-La/SSB much stronger than normal pooled IgG. Moreover, dsDNA but not RNA blocked these interactions. In addition, Ro/SSA and La/SSB but not $U_1$RNP blocked these same interactions. The results show that in sera with anti-RoiSSA and anti-La/SSB, there are subpopulations of these antibodies that bind and mask anti-dsDNA. It is hypothesized that these anti-Ro/SSA and anti-La/SSB are anti-idiotypes to idiotypes on anti-dsDNA and both mask and downregulate these anti-dsDNA antibodies.

MATERIALS AND METHODS

Serum samples

Sera were obtained from five patients with precipitating anti-Ro/SSA alone and eight with both anti-Ro/SSA and anti-La/SSB precipitins. These were selected from patients who at no time in their course had antibodies to dsDNA demonstrated in their sera by the Crithidia technique. Sera from patients with either anti-Ro/SSA precipitins alone or both anti-Ro/SSA and anti-La/SSB had either SLE, subacute cutaneous lupus erythematosus (SCLE), or Sjogren's syndrome. SLE patients were diagnosed on the basis of the revised ARA criteria.

Purified Ro/SSA and La/SSB

Bovine Ro/SSA and La/SSB proteins were purified from bovine liver or spleen tissue, according to established methods (Yamagata, et al., *J. Clin. Invest:*. 74:625–633 (1984)). Briefly, the supernatant of centrifuged bovine liver homogenate was mixed with an equal volume of DE-52 anion exchange resin previously equilibrated with mM phosphate buffer (pH 7.2). The DE-52 was washed with PBS and eluted with 1.0 M NaCl in mM phosphate buffer (pH 7.2). The eluted extract was applied to an anti-Ro/SSA affinity column. The Ro/SSA absorbed extract was then passed through an anti-La/SSB affinity column for isolation and purification of the 48 KD La/SSB protein. The final affinity-purified La/SSB protein was free of contaminating Ro/SSA protein by analysis in ELISA and immunoblots with monospecific anti-Ro/SSA antibodies.

Method of absorption by Ro/SSA or La/SSB

Five anti-RoISSA sera and eight anti-Ro/SSA and anti-La/SSB sera were absorbed by purified bovine Ro/SSA and La/SSB. Two and one-half microliters of serum was transferred to a centritube containing 10 μl (15 μg) of either Ro/SSA or La/SSB antigen. The tube was incubated for 2 hr at room temperature (RT), vortexing every 15 min. The absorption tube was then spun min at 5 at 14,000 rpm. Before use, the supernatant was brought to a final dilution of 1:100 by adding 237 μl buffer. Absorbed sera and unabsorbed sera were studied by Western blot with Molt-4 extract and anti-dsDNA ELISA.

From the same sera, IgG was isolated by DE-52 column chromatography and HPLC purification. Purified IgG also was absorbed by bovine Ro/SSA and La/SSB in a manner similar to the way whole serum was absorbed.

Western blot

Western blotting with Molt-4 extract was performed in a 15% SDS-polyacrylamide gel followed by electrotransfer to nitrocellulose in 20% methanol-tris-glycine buffer, pH 8.3. After transfer, nitrocellulose paper was cut into strips and blocked with 5% nonfat dry milk in 0.01 M Tris-HC1, 0.15 M NaCl, TWEEN® 20 (detergent), pH 8. 0 (TBST) for 30 min at RT. Serum or IgG samples were made in the blocking solution and strips were incubated in the sample dilution at RT for 30 min. After washing four times with TBST, strips were incubated in the sample dilution at RT for 30 min. After washing four times with TBST, strips were incubated with alkaline phosphatase conjugate (Sigma Chemical Co.) in the blocking solution for 30 min at RT. After incubation with conjugate and washing four times with TBST, strips were developed with NBT/BCIP substrate.

Anti-ds/DNA ELISA

One hundred fifty microliters of a protamine sulfate solution at 0.5 mg/ml in distilled water (negative Millon test, histone free, Sigma Chemical Co.) were introduced into each well of an IMMULON® microtiter plate and left for 2 hr at RT (Rupin, et al., *J. Immnunol. Methods* 160:245–252 (1993)). After three washes, each well was blocked with 150 μl of 10% adult bovine serum in PBS (10% ABS) After a 1-hr incubation at RT, the blocking solution was poured off and the plate rinsed three times with PBS containing 0.05% TWEEN® 20(PBT). Sera were diluted in 10% ABS at 1:100 and incubated for 2 hrs at RT, and plates were washed three times with PBT. Fifty microliters of goat anti-human IG-AP (Sigma Chemical Co.) were added and completed with the addition of paranitrophenyl phosphate, and the OD at 405 was determined with the Dynatech scanner.

Preparation of -IgG and IgG anti-dsDNA antibodies

The IgG fraction from an anti-Ro/SSA serum (No. 1) and three anti-La/SSB and anti-Ro/SSA (No. 2, 3, 4) sera were prepared by chromatography on DE-52 and protein A sepharose (Sigma Chemical Co.). Cellulose with coupled dsDNA was purchased from Sigma Chemical Company. Purified IgG from either DEAE or Protein A was passed through the dsDNA affinity column. The column was washed with TBS buffer, and bound protein was then eluted with 3 M $MgCL_2$. The specificity of the effluents and eluates was further determined by anti-dsDNA ELISA with titration of anti-dsDNA activity inhibition of this activity by dsDNA as well as RNA as a control.

Preparation of IgG anti-Ro/SSA and anti-La/SSB antibodies

Bovine Ro/SSA and Bovine La/SSB protein-SEPHAROSE® 4B (agarose bead) affinity columns were prepared. One patient's IgG (No. 1) with anti-Ro/SSA that was absorbed first.with the dsDNA cellulose column was passed through the Ro/SSA affinity column. Three patients' IgG (No. 2, 3, 4) with anti-La/SSB and anti-Ro/SSA that were absorbed with the dsDNA cellulose column were separately passed through the La/SSB affinity column. The columns were washed with TBS buffer, and bound antibodies were then eluted with 3 M MgCl. The eluates were dialyzed against 0.02 M TBS. Purified anti-Ro/SSA and anti-La/SSB antibodies were tested with. ELISA and Western blot for their specific antigenic activity.

Preparation of IgG $F(ab)_2$ fragments $F(ab)_2$ fragments were prepared separately from purified IgG anti-dsDNA, IgG anti-Ro/SSA, IgG anti-La/SSB (No. 1, 2, 3, 4) and normal IgG. IgG was digested by pepsin (Sigma Chemical Co.) (Nisonoff, et al. Arch. Biochem. Bioshys. 89:230–244 (1960)) and separated from uncleaved IgG and Fc fragments by sequential chromatography on SEPHADEX® G-100 (acrylamide bead) and protein A-SEPHAROSEO (agarose bead). Purified IgG $F(ab)_2$ was shown to be free of residual Fc by ELISA using goat anti-human Fc antibodies.

Inhibition of anti-dsDNA activity by IgG anti-Ro/SSA or anti-La/SSB (Competitive ELISA for idiotype expression)

Inhibition experiments were performed with various concentrations of anti-dsDNA antibodies. Each IgG anti-dsDNA fraction was incubated with increasing concentrations of IgG anti-Ro/SSA or anti-LaISSE, or IgG anti-Ro/SSA or IgG anti-La/SSB $F(ab)_2$ fragments isolated from the same individual's serum for 2 hr at RT. Residual anti-dsDNA activity was measured in the dsDNA ELISA. The inhibitor activity of IgG antiRo/SSA or IgG anti-La/SSB was calculated as follows:

$$1 - \frac{\text{antibody activity in test sample with added inhibitor}}{\text{antibody activity in control sample}} \times 100$$

Anti-dsDNA antibody activity in control samples was that contained in samples that had been incubated with PBS in the absence of IgG antiRo/SSA or anti-La/SSB or their $F(ab)_2$ fragments.

ELISA for detection of anti-idiotype activity in purified IgG antiLa/SSB and anti-Ro/SSB antibodies A 96-well ELISA plate was divided into two parts. One-half was coated with IgG anti-dsDNA $F(ab)_2$ (4 µg/ml) and the other half was coated with the same concentration of normal IgG F(ab)2. Absorptions of IgG anti-$F(ab)_2$ antibodies for each IgG anti-Ro/SSA and anti-La/SSB (No. 1, 2, 3, 4) with normal Cohn FII were performed by passing the antibody solutions over a Cohn FII $F(ab)_2$ affinity column. After absorption, IgG anti-Ro/SSA or IgG anti-La/SSB was applied to both sides of the plate, and the binding of IgG was detected by an alkaline phosphatase goat anti-human IgG Fc fragment specific conjugate (Sigma Chemical Co.). The idiotype levels in each individual anti-Ro/SSA and anti-La/SSB IgG were calculated by subtracting the binding of IgG anti-Ro/SSB or anti-La/SSB to control normal IgG $F(ab)_2$-coated wells from the binding of the anti-Ro/SSA or anti-La/SSB to anti-dsDNA $F(ab)_2$ coated wells. The results were then expressed as a percentage.

Competitive ELISA for antigen binding site idiotype expx-ession

The inhibition of anti-Ro/SSA or anti-La/SSB IgG binding to anti-dsDNA antibodies by the appropriate antigens was performed using a microtitre plate coated with $F(ab)_2$ fragment of anti-dsDNA IgG (No. 1, 2, 3, 4) (4 µg/ml). Serial dilutions of dsDNA or RNA (as a control) in PBS were added to the plates and incubated for 1 hr. Without removing the antigen solutions, each individual anti-Ro/SSA (No. 1) or anti-La/SSB (No. 2, 3, 4) antibody solution (same concentration) was added and incubated for an additional 1 hr at RT.

In reciprocal experiments, anti-Ro/SSA (No. 1) or anti-La/SSB (No. 2, 3, 4) IgG $F(ab)_2$ were used to coat plates. After blocking, serial dilutions of affinity-purified RoISSA, La/SSB and U,nRNP antigens (the latter as a control) in PBS were added and incubated for 1 hr. Without removing the antigen, each individual anti-dsDNA antibody preparation (No. 1, 2, 3, 4) was added and incubated for an additional 1 hr at RT. In both of the above cases, the experiments were completed by washing followed by the addition and incubation of an anti-Fcy conjugate for 1 hr at RT. After washing, this was followed by the substrate PNPP. After an appropriate length of incubation, the O.D. was read at 405 nm by a Dynatek scanner.

RESULTS

Absorption of anti-Ro/SSA sera lacking anti-dsDNA activity by bovine Ro/SSA unmasks IgG antibody activity to the A and D proteins in Western blot. Five sera from patients with precipitating anti-Ro/SSA antibodies, none of whom had measurable antibodies to dsDNA by the Crithidia assay, were absorbed with affinity-purified Ro/SSA. After absorption, the 60 kD Ro/SSA band in Western blot disappears (from sera 1 and 4), and there is the appearance of two new bands at 34 kD and 16 kD when the absorbed serum is used to probe Molt-4 proteins.

As a control, the same five anti-Ro/SSA sera were absorbed with La/SSB. La/SSB absorption had no effect on these sera except for serum 3 in which absorption removed subprecipitating amounts of anti-La/SSE activity (48 kD) with the appearance of anti-A and -D activity in the absorbed serum lane for serum 3.

Absorption of anti-La/SSB by LA/SSB unmasks IgG antibody activity against the A and SnRNP proteins Eight sera with anti-LaISSB precipitins were absorbed with affinity-purified La/SSB. After absorption, the 50 kD La/SSB band in Western blot disappears or becomes weaker, and there is the appearance of two new bands (34 kD and 16 kD). Three anti-La/SSE sera absorbed with La/SSB, after absorption showed the unmasking of antibody activity for dsDNA in ELISA as seen in Table 4. This absorption was also performed with IgG purified from an anti-La/SSB and anti-Ro/SSA serum with DE-52 and HPLC purification. The results show that IgG absorbed by bovine La/SSB unmasked anti-A and -D protein activity in Western blot and anti-dsDNA activity in ELISA. It is also seen that there is a significant but much smaller increment of activity against native URNP in ELISA for these three sera. Interestingly, while these three sera showed this unmasking effect of anti-dsDNA antibody activity, five other La/SSB sera absorbed with La/SSB did not show this activity.

TABLE 4

Antibody Activity to dsDNA and U$_1$RNP Unmasked After Absorption of Anti-La-SSB Sera with Purified La/SSB.

| Serum | DNA Absorbed | ELISA Unabsorbed | U$_1$RNP Absorbed | ELISA Unabsorbed |
|---|---|---|---|---|
| Bop | .720 | .000 | .598 | .363 |
| 1285 | .250 | .000 | .222 | .203 |
| 1123 | 1.362 | .252 | .609 | .401 |
| Mean ± S.D. | .777 ± .556 | .084 ± .146 | .476 ± .220 | .256 ± .093 |

Five other anti-La/SSB sera absorbed with La/SSB showed no antibody activity on either the DNA ELISA or the U$_1$RNP ELISA. All sera used at a 1/100 dilution.
Note that the increment of antibody activity for anti-nDNA (mean absorbed - mean unabsorbed) is .693 while for anti-U,RNP activity is much smaller being .200.

Figure 1B:
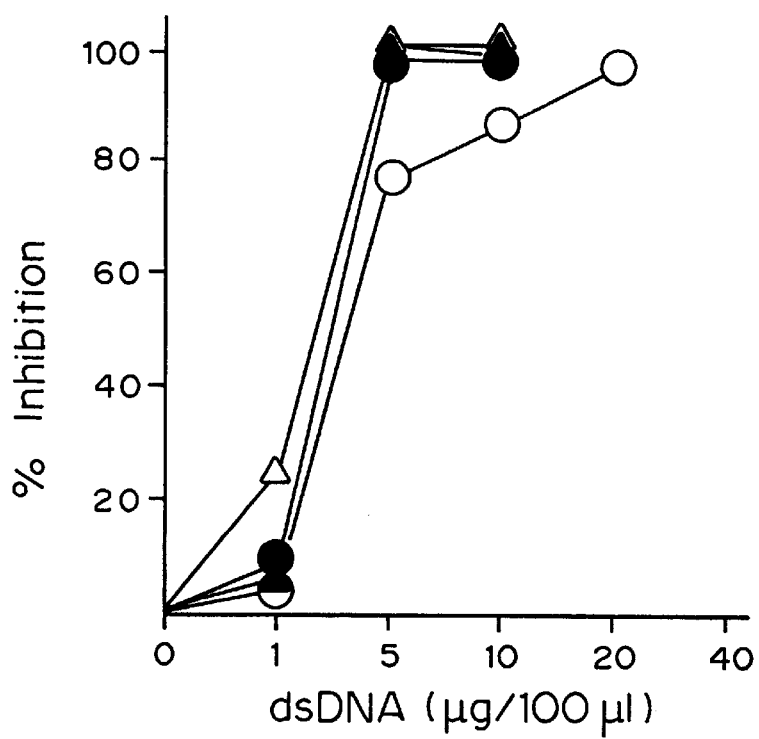

Unmasking of anti-dsDSNA antibodies from anti-Ro/SSA and anti-La/SSB patients IgG with dsDNA cellulose column An anti-Ro/SSA IgG (No. 1) and three anti-La/SSB and anti-Ro/SSA IgG preparations (No. 2, 3, 4) were separately passed over dsDNA cellulose columns. Isolation of anti-dsDNA antibodies was measured by ELISA, and the same concentration of isolated IgG was compared to whole serum IgG for its anti-dsDNA activity. The measurements show that the dsDNA cellulose column unmasks anti-dsDNA activity in these sera. The anti-dsDNA activity of these unmasked anti-dsDNA antibodies can be inhibited by dsDNA antigen as shown by FIGS. 1a and 1b. The effluents and eluates from the dsDNA column were tested by Western blot with Molt-4 cell extract and showed that two bands appear in the eluates. When eluates were mixed with dsDNA (50 μg/ml) and assayed in Western blot, anti-A (34 kD) and anti-D (16 kD) bands are largely inhibited in western blot. The 50 kD La/SSB band is unaffected by the addition of dsDNA as are other unidentified bands.

Inhibition of anti-dsDNA activity by autologous IgG anti-Ro/SSA and anti-La/SSB

Figure 2:
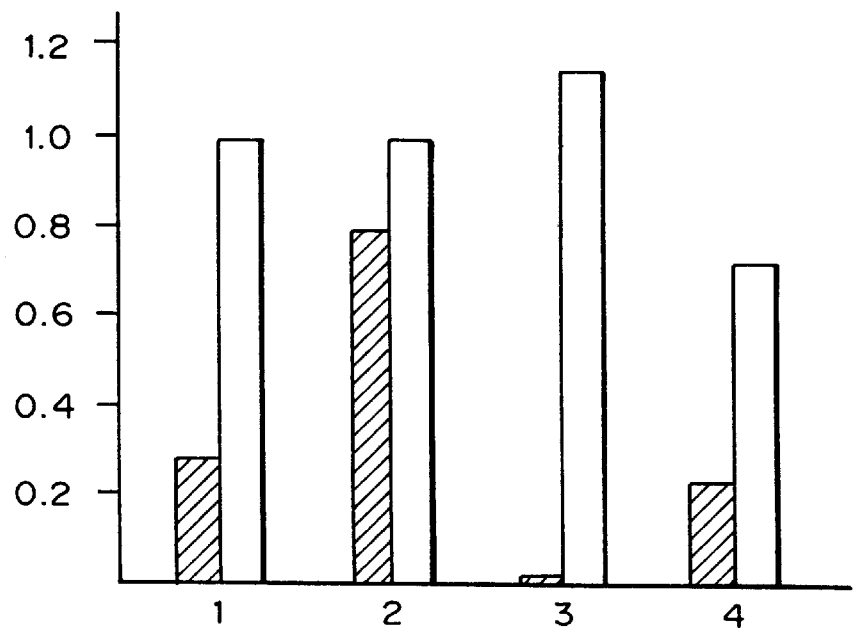
FIG. 2 is a graph showing inhibition by anti-Ro/SSA IgG F(ab)$_2$ or anti-La/SSB IgG F(ab')$_2$ of IgG anti-dsDNA preparations isolated from the sera of four patients with masked autoantibodies to dsDNA. Each patient's IgG anti-dsDNA was incubated with increasing amounts of F(ab)$_2$ fragments respective autologous anti-Ro/SSA IgG and anti-La/SSB IgG 2W antibody preparations.

The ability of anti-Ro/SSA IgG to inhibit autologous anti-dsDNA activity was examined by incubating anti-Ro/SSA IgG (No. 1) F(ab)$_2$ fragments with isolated IgG (No. 1) anti-dsDNA. The anti-La/SSB IgG (No. 2, 3, 4) fragments were also separately incubated with autologous IgG anti-dsDNA. Maximal inhibition of anti-dsDNA activity ranged from 56 to 76% and occurred at similar weight ratios between patient's IgG anti-dsDNA, IgG anti-Ro/SSA and IgG anti-La/SSB, as shown by FIG. 2. The results suggest that inhibition of anti-dsDNA activity by autologous IgG anti-Ro/SSA and IgG anti-La/SSB are as effective quantitatively as is the inhibition of anti-dsDNA antibodies activity by dsDNA antigen.

Figure 3:
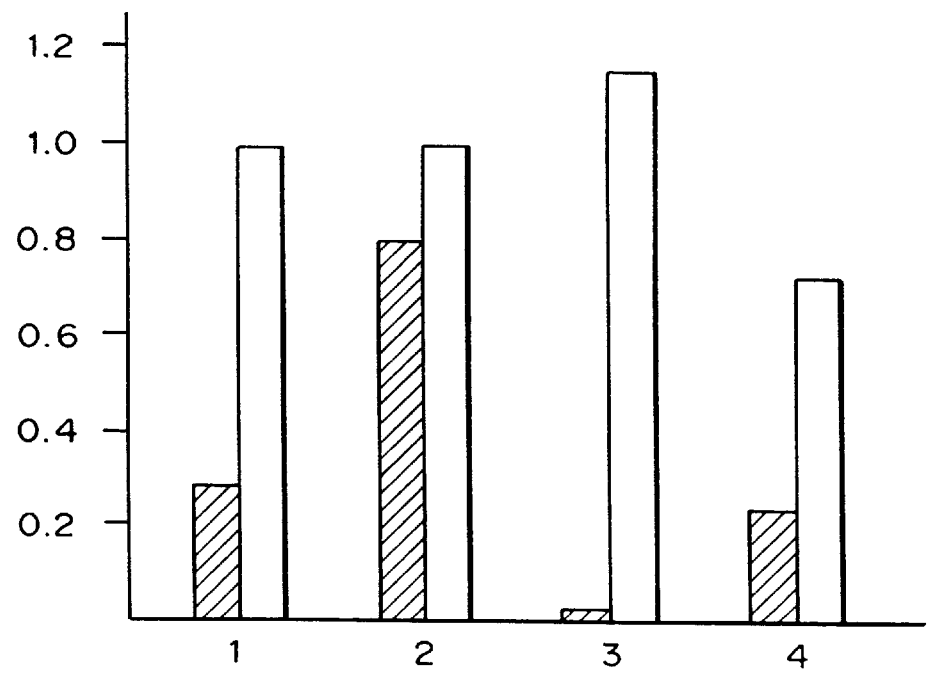
FIG. 3 is a graph of the anti-Idiotype levels of anti-Ro/SSA IgG and antiLa/SSB IgG. Comparative binding of normal IgG F(ab)$_2$ and IgG anti-dsDNA F(ab')$_2$ with respective autologous anti-Ro/SSA or anti-La/SSB IgG.

Expression of the anti-idiotype on anti-dsDNA immunoglobulins in reactivity with autologous purified anti-Ro/SSA and anti-La/SSB antibodies FIG. 3 shows the level of expression of anti-idiotype activity on anti-Ro/SSA IgG (No. 1) and anti-La/SSB IgG (No. 2, 3, 4). The level of anti-idiotype in the each individual anti-Ro/SSA IgG and anti-La/SSB IgG was calculated by subtracting the binding of IgG antiRo/SSA or anti-La/SSB to control normal IgG F(ab)$_2$-coated wells from the binding to autologous anti-DNA IgG F(ab)$_2$-coated wells in ELISA.

The results show that anti-Ro/SSA IgG binding to autologous anti-dsDNA IgG F(ab)$_2$, anti-idiotype level is 71%, No. 2 anti-La IgG binding autologous anti-dsDNA IgG F(ab)$_2$, anti-idiotype level is 24%, No. 3 anti-idiotype level is 98%, and No. 4 anti-idiotype level is 65%. These results show that individual patients' IgG with anti-Ro/SSA and anti-La/SSB manifest different anti-idiotype levels.

Inhibition of the idiotype-anti-idiotype reactions of anti-dsDNA with purified TgG anti-Ro/SSA and IgG anti-La/SSB with specific antigens One anti-Ro/SSA IgG preparation and two IgG anti-La/SSB preparations (No. 3, 4) were used to test the ability of the cognate antigens to inhibit their binding to anti-dsDNA antibodies. The rationale for this assay was that dsDNA, Ro/SSA, or La/SSB antigens, respectively, should be able to block the binding of IgG anti-Ro/SSA or IgG anti-La/SSB, respectively, to anti-dsDNA IgG idiotypic structures in the antibody binding sites. IgG anti-Ro/SSA was prevented from binding to anti-dsDNA antibodies by dsDNA; an inhibition of 50% required approximately 10 μg dsDNA. RNA was used as a control, which was ineffective in inhibiting this interaction. IgG anti-La/SSB was also inhibited from binding to autologous anti-dsDNA IgG by similar concentrations of dsDNA but not RNA.

Anti-Ro IgG F(ab)$_2$-coated plates were also used and the binding of autologous anti-dsDNA IgG tested. It was inhibited from binding to anti-Ro/SSA IgG by small concentrations of Ro/SSA protein, using U$_1$RNP as control which was ineffective. In similar experiments with anti-La/SSB IgG F(ab)$_2$-coated plates, autologous antidsDNA IgG was prevented from binding to anti-La/SSB IgG by La/SSB protein but not U$_1$RNP protein. Thus, these reactions reflect the participation of the binding site of antidsDNA, anti-La/SSB, and anti-Ro/SSA in these interactions as evidenced by the ability of antigens to specifically inhibit the interactions.

It is surprising to find that absorption of sera with only anti-Ro/SSA with purified bovine Ro/SSA or that absorption of anti-Ro/SSA and anti-La/SSB sera with bovine La/SSB, leads to the appearance of two new bands (34 kD and 16 kD) in Western blot in the absorbed sera. In parallel with the appearance of anti-A and -D activity, three of the anti-La/SSB sera absorbed with La/SSB exhibited an increment of antibody activity for dsDNA in ELISA. In addition to these experiments with absorbed sera, study of one anti-Ro/SSA serum and three anti-La/SSB sera when passed over dsDNA cellulose columns could unmask IgG anti-dsDNA activity measured in ELISA. Eluates from these dsDNA columns in addition to their anti-dsDNA activity bound 34 kD and 16 kD bands in Western blot. These unmasked anti-dsDNA reactions in both cases can be inhibited by dsDNA antigen.

Incubation of unmasked IgG anti-dsDNA with autologous anti-Ro/SSA or anti-La/SSB IgG F(ab)2 resulted in a dose-dependent inhibition of anti-dsDNA activity. Such data suggest that the interaction between anti-dsDNA IgG and anti-La/SSB IgG or anti-Ro/SSA IgG occurred within or near the antigen-combining site. Further data implicating the binding sites of the anti-dsDNA as well as the inhibitory properties of the anti-Ro/SSA and anti-La/SSB antibodies comes from the ability of the cognate antigen to specifically block these interactions of some anti-Ro/SSA and anti-La/SSB antibodies to bind anti-dsDNA, as demonstrated by data showing that dsDNA but not RNA blocked anti-Ro/SSA IgG or anti-La/SSB IgG binding to autologous anti-dsDNA IgG, and that Ro/SSA or La/SSB antigen blocked anti-Ro/SSA IgG or anti-La/SSB IgG binding to autologous anti-dsDNA antibodies. $U_1NP$ was a control and did not block these interactions.

The results strongly suggest that some -patients with IgG anti-Ro/SSA or anti-La/SSB contain anti-Ids reactive with idiotypes expressed on autologous anti-dsDNA antibodies. Anti-Ids have been classified into four groups (Cavacco, et al., *J. Autoimmun.* 7:537–548 (1994)). Anti-Id (a) recognizes idiotypes distinct from the antigen-combining site, ltusually in the framework region. Anti-Id (b) 211- recognizes idiotypes within the antigen-combining site and bear the internal image of the nominal antigen.

Anti-Id C) recognize idiotypes within or near the antigen-combining site and therefore are antigen inhibitable because of steric interference; however, they do not mimic the three-dimensional structure of the nominal antigen. Anti-Id (d) recognize determinants shared by the antibodies and by the nominal antigen. According to this classification, the inhibition assays performed in this study suggest that most of the anti-Ids to anti-dsDNA are antigen-inhibitable and are likely related to idiotypic structures within the antigen binding site and are mainly type b as described above.

Anti-Ids may play an important role in patients who spontaneously recover from autoimmune diseases. In fact, autologous anti-Id against autoantibodies have been demonstrated in the sera of patients in remission from a variety of autoimmune disorders (Abdou, et al., *J. Clin. Invest.* 67:1297–1304 (1980); Lefvert, *J. Immunol.* 13:493–497 (1981); Dwyer, et al., *Nature* 301:611–614 (1983); Paquali, et al., *Clin. Exp. immunol.* 55:281–286 (1984); Sikorska, *J. Immunol.* 137:3786–3795 (1986); Sultan, *Proc. Natl. Acad. Sci. USA* 84:838–831 (1987); Muryoi, et al., *Clin. Exp. Immunol.* 71:67–72 (1988); Shoenfeld and Isenberg, *Sem. Arthritis Rheum.* 16:245–252 (1987);

Silvestris, et al., *Arthritis Rheum.* 27:1387–1396 (1984)).

Example 8: Definition of Reactive Epitope Which Mediates Antigenic Relationship Between SnRNP A and D Proteins and Development of Immunoassay In order to develop the appropriate immunoassays and possible immunotherapies based on tolerance induction, it is necessary to determine the structure of the dominant epitopes in the SnRNP A and D proteins which determine the cross reaction between anti-dsDNA and the denatured SnRNP A and D proteins.

Since these reactivities are seen thus far only in Western blot, the epitopes are assumed to be short linear amino acid sequences; i.e., they are so-called sequential determinants. The A and D sequence can be screened by the Pepscan method (Geysen, H. M., Meloen, R. H. and Barteling, S. *J., Proc. Nat. Acad. Sci. USA,* 81:3998–4002, 1984) which is adequate for identification of sequence dependent epitopes which are bound by isolated polyclonal human anti-dsDNA, monoclonal murine or human anti-dsDNA. Alternatively, or in addition, one can look for epitope(s) shared between the A and D proteins by visually scanning the A and D sequences. There are three octapeptide sequences which share at least a tetrapeptide sequence ts conservative substitutions such as Ileu for Arg as shown in Table 5.

TABLE 5

Paired A and D Octapeptides to a Recognized Epitope Which are Antigenic for Lupus Sera.

| | | | |
|---|---|---|---|
| 1 | | | |
| | | 5 | 12 |
| D | Arg Phe Leu | MetLysLeuSer | His |
| | (Seq. ID No. 1) | | |
| | 275 | | 282 |
| A | MetLysIleuSer | Phe Ala Lys Lys | |
| | (Seq. ID No. 2) | | |
| 2 | | | |
| | 41 | | 48 |
| D | LysAlaValLys | Met Thr Leu Lys | |
| | (Seq. ID No. 3) | | |
| | 16 | | 23 |
| A | Asn Leu Asn Glu | LysIleuLysLys | |
| | (Seq. ID No. 4) | | |
| 3 | | | |
| D | Lys SerLysLysArgGlu | Ala Val | |
| | (Seq. ID No. 5) | | |
| | 105 | | 112 |
| A | AspArgLysArgGlu | Lys Arg Lys | |
| | (Seq. ID No. 6) | | |

These paired octapeptides are reasonable candidates for sharing an epitope(s) and the following strategy is proposed in parallel with the overlapping peptide strategy. These six octapeptides can be synthesized using known methodology. These are excellent reagents for coating ELISA plates and can also be conjugated to solid supports by activating the carboxly group with carbodiimide and attaching the active-ate peptide to sepharose for affinity chromatography, using reagent manufacturer's instructions. Such MAP peptides have also been used successfully to immunize animals.

For example, peptides can be synthesized in bulk (milligram quantities) on a branching poly-lysine (Maps™, Applied Biosystems, CA) backbone. Maps™ is a pyramid of fifteen lysines upon which eight peptides are added to form a multiple antigenic structure. These reagents allow the screening of large numbers of lupus and normal control sera.

These octapeptides are then used to coat Immunlon™ microtiter plates (Costar, Cambridge, Mass.) and screened for binding to murine or human monoclonal anti-dsDNA antibodies or human polyclonal anti-dsDNA antibodies in ELISAs. If they are bound by one or both members of the pair, the ability of one peptide to inhibit the reactivity of the other with the affinity purified anti-dsDNA will then be tested.

These two approaches: (1) screening the entire sequence by the Pepscan™ method, and (2) testing the pairs of known epitopes with sequence similarity in A and D can be used to identify the 2t. cross reactive epitope(s) on the A and D proteins which cross react with either murine or human anti-dsDNA. Competition experiments done by methods well known to those skilled in the art should establish the relative affinity of dsDNA, the A and D proteins, and the reactive peptides.

Example 9: Development of Peptide- or Protein-based Immunoassay for Clinical Use in Diagnosis and Prognosis Once the reactive peptide epitope is delineated, this can be used as a coating antigenic reagent (e.g., as a MAP™ peptide) in a solid phase based ELISA. The assay is first validated against the Western blot data. It is expected that the ELISA will detect all of the anti-dsDNA antibodies that bind the SnRNP A and D proteins in Western blot since ELISA is 10 to 100 times more sensitive than Western blot. An alternative strategy is to use Western blotting with crude extract as a screening assay.

If the two bands are seen, their specificity would be assured by inhibiting their development by 50 μg/ml DNA as described in Example 1.

This method is slow, cumbersome, and non-quantitative. A second strategy involves development of an ELISA based assay in which coats are plated with recombinant A and recombinant D; the reactions should be nearly identical. This method is simple, quantitative, easy to automate, and quality control would be straightforward.

By far, the best strategy is to identify the peptide epitope (s) and then construct quantitative ELISA's which will be specific, quantitative, simple, easy to automate, and the antigen is synthesized by established chemical methods, and thus in infinite supply.

For clinical purposes a test would still have to be done for anti-dsDNA since not all anti-dsDNA cross reacts with A and D, yet all anti-dsDNA is specific for SLE. A hypothetical Table 6 shows how the tests would work and what diagnostic information and prognostic information would flow from the performance of the tests.

For the purposes of the table, the anti-dsDNA test used would be the crithidia assay, but there are other tests which could also be used. An ELISA for anti-dsDNA is easy to design as a kit in which anti-peptide epitope and anti-dsDNA are measured in the same assay.

TABLE 6

Use of Detection of Antibody to dsDNA and Cross Reactive Epitope on SnRNP.

| Diagnosis | Disease Activity | Prognosis | Anti-dsDNA Crithidia | Anti-A & D Peptide |
|---|---|---|---|---|
| Normal | 0 | 0 | 0 | 0 |
| SLE | 4+ | Severe Disease | + | + |
| SLE | tr to 1+ | Mild | 0 | + |
| SLE | tr to 1+ | Mild | + | 0 |

These tests would not detect all SLE patients, since at most 90% of active untreated SLE patients have anti-dsDNA which includes IgG anti-dsDNA. However, they measure a very important facet of anti-dsDNA; i.e., which ones are likely to cause or be associated with active severe disease and which ones indicate a more serious prognosis with the clinical correlates of anti-dsDNA, especially nephritis.

Example 10: Development of Peptide- or Protein-based Immunoassay for Clin.ical Use in Diagnosis and Prognosis The assays and methods of treatment described herein are based on the interpretation of the foregoing data showing that absorption of anti-La/SSB and anti-$U_1$RNP are in an idiotypic network relationship- Thus, anti-La/SSB is an anti-idiotype of anti-A and D (or vice versa), anti-Ro/SSA is an anti-idiotype of anti-A and D (or vice versa) and anti-$U_1$RNP is an anti-idiotype to anti-A and D or vice versa.

The studies reported above used anti-$U_1$RNP sera not reactive with A or D proteins in Western blot before absorption. The experiments were done by absorption in the fluid phase with La/SSB or $U_1$RNP added to small amounts of serum, generally between 10 and 15 μg La/SSB, Ro/SSA or $U_1$RNP added to 2.5 μl serum or 4.5 mg pure antigen/ml serum which is a large antigen excess. After 2 hours incubation the material is spun down and the supernatant is brought to 250 μl with PBS. Thus the serum reaches a final dilution of 1:100, at which point it is used to develop Western blots and is compared to unabsorbed sera.

These experiments are based on serological tests without separation and purification of the reactants; i.e., the anti-La/SSB, the anti-Ro/SSA or the anti-$U_1$RNP on the one hand and the unmasked anti-A and D antibodies on the other hand, which also apparently have anti-dsDNA activity in many instances.

The most rigorous way to do the absorption so that free antigen cannot in any way complicate the interpretation of the experiments or introduce artifacts is to covalently bind La/SSB, Ro/SSA or U3RNP to Sepharose™ and then absorb the sera with La/SSB or $U_1$RNP coated beads. This is done until it leads to unmasking of anti-A and D reactivity in Western blot.

Once anti-La/SSB or Ro/SSA antibodies are isolated they can be then studied for their reactivity with isolated unmasked anti-A and D or affinity purified anti-dsDNA in the following way. The isolated unmasked antibody with anti-A and D activity or isolated affinity purified anti-dsDNA can be pepsin digested and used to coat Immunlon™ plates. Reactivity of whole anti-La/SSB or anti-Ro/SSA with plates coated with pepsin digested anti-A and D ($Fab_2$) can be studied by detection with a T chain specific antibody conjugated with alkaline phosphatase. There will only be color development after addition of substrate if the whole IgG anti-La/SSB binds to the plate. Standard variations of this technology can be used to screen large numbers of relevant related or unrelated antibodies.

Anti-La/SSB, anti-Ro/SSA or anti-$U_1$RNP antibodies affinity isolated in this way can be rigorously tested for their inhibitory reactivity with anti-dsDNA reacting with dsDNA coated plates or in inhibiting anti-dsDNA reacting in the Crithidia assay without interference by excess free antigen.

The rationale for isolating the anti-La/SSB, anti-Ro/SSA and anti-$U_1$RNP antibodies as well as the unmasked antibodies is to permit the rigorous quantitative study of the interaction between and among such antibodies. This also avoids potential artifacts being introduced by not separating all of the reactants and relying completely on serological methods. It also permits the study of the interaction of these reactants between different patients in order to identify a broadly cross reactive anti-La/SSB or a anti-$U_1$RNP that can be used to down regulate anti-dsDNA in unrelated patients.

Modifications and variations of the present invention will be obvious to those skilled in the art and are intended to come within the scope of the appended claims.

We claim:

1. A method for determining whether it is more likely than not that a lupus patient will develop severe disease and nephritis comprising determining if the patient produces anti-double stranded DNA antibodies that are cross-reactive with double stranded DNA and with denatured A SnRNP protein or D SnRNP protein.

2. The method of claim 1 further comprising determining if the patient produces anti-La/SSB, anti-Ro/SSA or anti-U₁RNP antibodies that are crossreactive with both anti-double stranded DNA and either denatured A SnRNP protein or D SnRNP protein.

3. An assay kit for determining whether it is more likely than not that a lupus patient will develop severe disease and nephritis comprising means for determining if the patient produces anti-double stranded antibodies that are crossreactive both with double stranded DNA and with denatured A and D SnRNP proteins, wherein the kit comprises as reagents: (1) double stranded DNA and (2) denatured A SnRNP protein, denatured D SnRNP protein, or both denatured A SnRNP protein and denatured D SNRNP protein.

4. The assay kit of claim 3 further comprising means for determining if the patient produces anti-La/SSB, anti-Ro/SSA or anti-UIRNP antibodies that are crossreactive with both anti-double stranded DNA and with denatured A SnRNP protein and D SnRNP protein.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

```
Arg Phe Leu Met Lys Leu Ser His
1               5
```

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

```
Met Lys Ile Ser Phe Ala Lys Lys
1               5
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
Lys Ala Val Lys Met Thr Leu Lys
1               5
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO

```
       (iv) ANTI-SENSE: NO (v) FRAGMENT TYPE: internal (xi) SEQUENCE DESCRIPTION: SEQ ID NO:4:

Asn Leu Asn Glu Lys Ile Lys Lys
1               5

(2) INFORMATION FOR SEQ ID NO:5:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

Lys Ser Lys Lys Arg Glu Ala Val
1               5

(2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

Asp Arg Lys Arg Glu Lys Arg Lys
1               5
```